United States Patent [19]

Eicher et al.

[11] Patent Number: 5,214,223
[45] Date of Patent: May 25, 1993

[54] METHOD OF PREPARING FLUORINE-CONTAINING ETHANE DERIVATIVES

[75] Inventors: Johannes Eicher, Garbsen; Karlheinz Fazniewscy, Lehrte; Werner Rudolph; Hans-Walter Swidersky, both of Hanover, all of Fed. Rep. of Germany

[73] Assignee: Kali-Chemie AG, Hanover, Fed. Rep. of Germany

[21] Appl. No.: 912,981

[22] Filed: Jul. 14, 1992

Related U.S. Application Data

[62] Division of Ser. No. 683,834, Apr. 11, 1991, Pat. No. 5,071,900.

[30] Foreign Application Priority Data

Apr. 12, 1990 [DE] Fed. Rep. of Germany ....... 4011789
Feb. 25, 1991 [DE] Fed. Rep. of Germany ....... 4105832

[51] Int. Cl.$^5$ .......................... C07C 17/00; B01J 31/00
[52] U.S. Cl. ..................................... 570/166; 502/150; 502/169; 570/165; 570/168
[58] Field of Search ........................ 570/165, 168, 166; 502/150, 169

[56] References Cited

U.S. PATENT DOCUMENTS

| | | | |
|---|---|---|---|
| 2,462,359 | 2/1949 | Calfee et al. | 260/653 |
| 3,810,948 | 5/1974 | Muessdoerffer et al. | 260/653.6 |
| 4,258,225 | 3/1981 | Feiring | 570/168 |
| 4,374,289 | 2/1983 | Van Der Puy et al. | 570/168 |
| 4,383,128 | 5/1983 | Van Der Puy et al. | 570/165 |

FOREIGN PATENT DOCUMENTS

| | | |
|---|---|---|
| 048544 | 3/1982 | European Pat. Off. |
| 297947 | 1/1989 | European Pat. Off. |
| WO89/12616 | 12/1989 | PCT Int'l Appl. |
| WO89/12617 | 12/1989 | PCT Int'l Appl. |

Primary Examiner—Werren D. Lone
Attorney, Agent, or Firm—Foley & Lardner

[57] ABSTRACT

A method of preparing fluorine-containing ethane derivatives using a catalyst mixture which comprises a metal halide and a sulfonic acid derivative is described. The method is particularly well suited for preparing $CF_3CHCl_2$ (R123) from perchloroethylene and for preparing $CF_3CH_2F$ (R134a) from trifluoroethylene.

8 Claims, No Drawings

METHOD OF PREPARING FLUORINE-CONTAINING ETHANE DERIVATIVES

This application is a division of application Ser. No. 07/683,834, filed Apr. 11, 1991 U.S. Pat. No. 5,071,900.

BACKGROUND OF THE INVENTION

This invention relates to a method for preparing fluorine-containing ethane derivatives corresponding to the formula $F_kH_nCl_{3-(k+n)}C$—$CZ^1Z^2F$, wherein, k, n, $Z^1$ and $Z^2$ have the meanings described below.

There is an increasing need for environmentally compatible halogenated hydrocarbons. Examples of such hydrocarbons have been found to include the fluorine-containing ethane derivatives which contain at least one hydrogen atom, for instance $CF_3CH_3$ (R143a), $CF_3CH_2Cl$ (R133a), and especially $CF_3CHCl_2$ (R123). However, the corresponding 1-fluoro or 1,1-difluoro compounds are also of interest, for instance the compounds $CFCl_2CHCl_2$ or $CF_2ClCHCl_2$, which are considered environmentally compatible and which can be used as refrigerants, solvents or propellants.

Industrially, such compounds are prepared by catalyzed halogen-fluorine exchange, particularly by chlorine-fluorine exchange, from correspondingly halogenated derivatives. The halogenated starting compounds used for this are, however, very inert with respect to halogen-fluorine exchange. Particularly for preparing higher fluorinated compounds, drastic process conditions are necessary. Despite such drastic conditions, for instance operation in the gaseous phase, the conversions are usually low. A further drawback of known methods is that the catalysts used, which are often very expensive, do not have a satisfactory life.

SUMMARY OF THE INVENTION

It is the object of the present invention to provide a method of preparing fluorine-containing ethane derivatives which is relatively easy to perform industrially.

Another object of the invention is to provide a method of preparing fluorine-containing ethane derivatives which produces a high conversion.

These and other objects are achieved by providing a method of preparing a fluorine-containing ethane derivative corresponding to the formula (I)

$$F_kH_nCl_{3-(k+n)}C—CZ^1Z^2F \qquad (I),$$

wherein $Z^1$ and $Z^2$ may be identical or different and represent hydrogen, fluorine, chlorine or bromine; k is 0, 1 or 2, and n is 2 or 3, said method comprising reacting a halogenated alkene or halogenated alkane starting compound with hydrogen fluoride in the presence of a catalyst system in the liquid phase at a temperature between 0° and 250° C., wherein hydrogen fluoride is present in said liquid phase in an at least equimolar quantity relative to said starting compound; the molar ratio of starting compound to catalyst system is from about 10:1 to 1:100; the catalyst system comprises a mixture of metal halide and a sulfonic acid derivative in a molar ratio of from about 100:1 to about 1:10; the metal halide is selected from the group consisting of niobium pentahalide, tantalum pentahalide, molybdenum pentahalide and mixtures thereof; the sulfonic acid derivative is selected from the group consisting of fluorosulfonic acid and perfluoro-lower alkane sulfonic acids with 1 to 4 carbon atoms, and the starting compound is a) a halogenated alkene corresponding to the formula (II)

$$F_kH_mCl_{2-(k+m)}C=CX^1X^2 \qquad (II),$$

wherein $X^1$ and $X^2$ may be identical or different and represent hydrogen, fluorine, chlorine or bromine, k has the meaning given above and m is 0, 1 or 2; or b) a halogenated alkane corresponding to the formula (III)

$$F_kH_nCl_{3-(k+n)}C—CY^1Y^2Y^3 \qquad (III),$$

wherein k and n have the above meanings; $Y^1$ and $Y^2$ may be identical or different and represent hydrogen, fluorine, chlorine or bromine, and $Y^3$ represents chlorine or bromine.

DETAILED DESCRIPTION OF PREFERRED EMBODIMENTS

The method according to the invention for preparing fluorine-containing ethane derivatives of the general formula (I)

$$F_kH_nCl_{3-(k+n)}C—CZ^1Z^2F \qquad (I),$$

wherein $Z^1$ and $Z^2$ may be identical or different and represent hydrogen, fluorine, chlorine or bromine; k is 0, 1 or 2 and n is 1, 2 or 3, comprises reacting a halogenated alkene or halogenated alkane as the starting compound with hydrogen fluoride in the presence of a catalyst system in the liquid phase at a temperature between 0° and 250° C., with the hydrogen fluoride being present in the liquid phase at least in an equimolar quantity, relative to the starting compound, the molar ratio of starting compound to catalyst system being between about 10:1 and 1:100; the catalyst system comprising a mixture of metal halide and a sulfonic acid derivative in a molar ratio of from about 100:1 to about 1:10; the metal halide being selected from the group consisting of niobium pentahalide, tantalum pentahalide, molybdenum pentahalide and mixtures thereof; the sulfonic acid derivative being selected from the group consisting of fluorosulfonic acid and perfluoro-lower alkane sulfonic acids having 1 to 4 carbon atoms, in particular trifluoromethane sulfonic acid, and wherein a) a compound corresponding to the formula (II)

$$F_kH_mCl_{2-(k+m)}C=CX^1X^2 \qquad (II),$$

wherein $X^1$ and $X^2$ may be identical or different and represent hydrogen, fluorine, chlorine or bromine, k is 0, 1 or 2, and m is 0, 1 or 2, is used as the halogenated alkene, or b) a compound corresponding to the formula (III)

$$F_kH_nCl_{3-(k+n)}C—CY^1Y^2Y^3 \qquad (III),$$

wherein k and n have the above meanings, $Y^1$ and $Y^2$ may be identical or different and represent hydrogen, fluorine, chlorine or bromine, and $Y^3$ represents chlorine or bromine, is used as the halogenated alkane.

Within the scope of the present invention, the total of k and n is 1, 2 or 3, and the total of k and m is 0, 1 or 2. Preferably in the starting compounds of Formulae II and III, k represents 0, and $X^1$, $X^2$, $Y^1$ and $Y^2$ represent fluorine, chlorine or bromine.

The method may be operated at pressures from about 1 to 100 bar (absolute) and at temperatures from about 0° to 250° C. The pressure and temperature are selected so that the reaction takes place in the liquid phase.

The ethane derivatives obtained in the method according to the invention differ from the starting compounds in that they carry at least one more fluorine atom. For each fluorine atom introduced into the substrate molecule in this manner, hydrogen fluoride preferably is used in a quantity which corresponds at least to the stoichiometrically required quantity. A larger excess of hydrogen fluoride, for instance up to fifteen times the stoichiometrically required quantity or more, may also be used for hydrogen fluoride (HF) addition and/or for halogen-fluorine exchange.

When preparing derivatives containing trifluoromethyl groups from unsaturated compounds, good results are achieved even if the quantity of hydrogen fluoride used corresponds to from one to ten times the stoichiometrically required quantity.

The quantity of hydrogen fluoride to be used may exceed this quantity, which is required for hydrogen fluoride addition and/or for the chlorine-fluorine exchange on the alkene or alkane. If metal halides which contain chloride or bromide are used as catalyst constituents, it is expected that these metal halides will be present in the reaction mixture in the form of metal pentahalides containing greater or lesser amounts of fluorine as a result of exchange of chlorine or bromine for fluorine. For instance, niobium pentachloride may be converted into compounds of the type $NbCl_{5-x}F_x$, niobium pentabromide may be converted into compounds of the type $NbBr_{5-x}F_x$, tantalum pentachloride into $TaCl_{5-x}F_x$, and tantalum pentabromide into compounds of the type $TaBr_{5-x}F_x$, where x is a number from 0 to 5. The same applies to the corresponding molybdenum halides. If therefore in a preferred embodiment niobium pentachloride or tantalum pentachloride is used as the metal halide, these may possibly be present in the reaction mixture in the form of partially fluorinated or fluorinated metal compounds.

The foregoing statement regarding the quantity of hydrogen fluoride to be used should therefore read in full: "For each fluorine atom introduced into the substrate molecule, hydrogen fluoride is advantageously used in a quantity which corresponds at least to the stoichiometrically required quantity, and additionally as much hydrogen fluoride as is required for any halogen-fluorine exchange of the metal halide." The statements made hereinafter concerning the stoichiometry of the hydrogen fluoride to be used for the addition of hydrogen fluoride and/or the halogen-fluorine exchange in the alkene or alkane are also to be understood correspondingly. For simplicity, these statements do not expressly mention each time that additional hydrogen fluoride may be necessary for any halogen-fluorine exchange of the metal halide.

In order to determine what amount of hydrogen fluoride is additionally necessary for this halogen-fluorine exchange, a person skilled in the art can react the metal halide to be used with hydrogen fluoride in advance. The quantity of hydrogen fluoride consumed and/or the quantity of hydrogen halide formed makes it possible to calculate the quantity of hydrogen fluoride needed in addition to that required for reacting the halogenated hydrocarbon used.

The following procedure is particularly simple and advantageous: the metal halide, for instance molybdenum pentachloride or pentabromide, niobium pentachloride or pentabromide, or tantalum pentachloride or pentabromide, is placed in a fluorination reactor, and hydrogen fluoride is added until no more hydrogen chloride or hydrogen bromide is produced. After the addition of the sulfonic acid derivative, the halogenated hydrocarbon which is to be fluorinated and the hydrogen fluoride required for the fluorination thereof are introduced into the catalyst mixture. In this case it is not necessary to supply additional hydrogen fluoride for the fluorination of the metal chloride or bromide.

It is advantageous for preparing lower fluorinated compounds, for instance $CHCl_2CCl_2F$ from $CHCl_2CCl_3$ or $CCl_2=CCl_2$, $CH_2ClCCl_2F$ from $CH_2ClCCl_3$ or $CHCl=CCl_2$, or $CH_3CCl_2F$ from $CH_3CCl_3$ or $CH_2=CCl_2$, to operate in the lower temperature range, for instance between 50° and 150° C. The degree of reaction can be monitored analytically, for example, by taking samples and analyzing them by gas chromatography.

In this case the high degree of reaction of the method according to the invention is advantageous.

Some examples of fluorine-containing ethane derivatives which can be prepared using the method of the invention together with a listing starting compounds which can be used and the stoichiometrically required quantity of hydrogen fluoride, are given in the following Table 1.

TABLE 1

| |
|---|
| $CCl_2=CCl_2 + HF \rightarrow CHCl_2CCl_2F$ |
| $CCl_2=CCl_2 + 3\ HF \rightarrow CHCl_2CF_3$ |
| $CHCl_2CCl_3 + 3\ HF \rightarrow CHCl_2CF_3$ |
| $CHCl_2CCl_2F + 2\ HF \rightarrow CHCl_2CF_3$ |
| $CHCl_2CClF_2 + HF \rightarrow CHCl_2CF_3$ |
| $CHCl=CCl_2 + 3\ HF \rightarrow CH_2ClCF_3$ |
| $CH_2ClCCl_3 + 3\ HF \rightarrow CH_2ClCF_3$ |
| $CH_2=CCl_2 + 3\ HF \rightarrow CH_3CF_3$ |
| $CH_3CCl_3 + 3\ HF \rightarrow CH_3CF_3$ |
| $CHF=CF_2 + HF \rightarrow CH_2FCF_3$ |

The advantages of the method according to the invention are especially evident in the preparation of higher fluorinated products. In the preparation of higher fluorinated products, such as the preparation of $CHCl_2CF_3$ from $CHCl_2CCl_3$, $CHCl_2CCl_2F$, $CHCl_2CClF_2$, $CCl_2=CCl_2$ or mixtures thereof; the preparation of $CH_2ClCF_3$ from $CH_2ClCCl_3$, $CH_2ClCCl_2F$, $CH_2ClCClF_2$, $CHCl=CCl_2$ or mixtures thereof; or the preparation of $CH_3CF_3$ from $CH_3CCl_3$, $CH_3CCl_2F$, $CH_3CClF_2$, $CH_2=CCl_2$ or mixtures thereof, it is advantageous to operate in the higher temperature range, for instance from 70° to 220° C. and at from 10 to 50 bar. Again, the degree of reaction can be monitored by analyzing samples taken from the reaction mixture.

The method of the invention is therefore particularly advantageous for preparing higher fluorinated compounds, in particular trifluoromethyl group-containing ethane derivatives corresponding to the formula $F_kH_nCl_{3-(k+n)}C—CF_3$ (Ia), in which k represents 0, 1 or 2 and n represents 1, 2 or 3.

This preferred embodiment of the method according to the invention is characterized in that for preparing a fluorine-containing ethane derivative corresponding to the formula (Ia)

$$F_kH_nCl_{3-(k+n)}C—CF_3 \qquad (Ia),$$

wherein k represents 0, 1 or 2, and n represents 1, 2 or 3, at a temperature from 0° to 250° C. and a pressure of 1 to 100 bar (absolute)

a) a halogenated alkene corresponding to the formula (II)

$$F_kH_mCl_{2-(k+m)}C=CX^1X^2 \qquad (II),$$

wherein k and m have the meanings given above, $X^1$ and $X^2$ represent fluorine, chlorine or bromine, is reacted with hydrogen fluoride, with the hydrogen fluoride being present in the reaction mixture in an amount corresponding to at least one-fold the quantity stoichiometrically required for the hydrogen fluoride addition and for the halogen-fluorine exchange on the alkene, or b) a halogenated alkane corresponding to the formula (III)

$$F_kH_nCl_{3-(k+n)}C-CY^1Y^2Y^3 \qquad (III),$$

wherein k and n have the above meanings; $Y^1$ and $Y^2$ are fluorine, chlorine or bromine, and $Y^3$ is chlorine or bromine, is reacted with hydrogen fluoride, with the hydrogen fluoride in the reaction mixture being present in an amount corresponding to at least one-fold the quantity stoichiometrically required for the halogen-fluorine exchange on the alkane.

The advantages of the method according to the invention become particularly apparent when the corresponding halogenated alkenes are used as the starting compound. The degree of conversion when using these compounds, which are actually very inert, is very high. The formation of polymers and of compounds produced by adding halogen instead of hydrogen fluoride, which is observed with other methods, is not observed, or is observed only to a negligible extent, in the method of the invention.

According to a preferred embodiment of the method of the invention, halogenated alkenes are used as the starting compounds. In a first reaction step, hydrogen fluoride addition compounds form initially. If it is intended to prepare lower fluorinated compounds which have valuable properties, for instance as solvents, these compounds are isolated from the reaction mixture. If it is intended to prepare higher fluorinated products, particularly ethane derivatives containing trifluoromethyl groups, the initially produced compounds can be isolated and fluorinated again. Advantageously, however, the hydrogen fluoride addition compounds produced initially in the first reaction step are not isolated, but are reacted in situ with additional hydrogen fluoride to produce the desired higher fluorinated products.

To prepare alkanes with a $CF_3$-group, fluorosulfonic acid is advantageously used as the sulfonic acid derivative.

Alkenes which are at least partially fluorinated also can be used as starting material. Thus, according to another preferred embodiment of the present invention, $CF_3CH_2F$ can be prepared by reacting trifluoroethylene with hydrogen fluoride in the presence of the catalyst system formed from the metal halide and sulfonic acid derivative. Surprisingly, polymerization of the alkene is not observed.

The method of the invention is outstandingly suitable for preparing $CHCl_2CF_3$ (R123). This very particularly preferred embodiment of the method of the invention is characterized in that for preparing $CHCl_2CF_3$ a) $CCl_2=CCl_2$ is reacted with hydrogen fluoride, with the quantity of hydrogen fluoride in the reaction mixture corresponding to at least one-fold the quantity stoichiometrically required for the hydrogen fluoride addition and for the chlorine-fluorine exchange on the alkene, or b) $CHCl_2CCl_3$, $CHCl_2CFCl_2$, $CHCl_2CF_2Cl$ or a mixture thereof is reacted with hydrogen fluoride, with the quantity of hydrogen fluoride in the reaction mixture corresponding to at least one-fold the quantity stoichiometrically required for the chlorine-fluorine exchange on the alkane.

The preparation of $CHCl_2CF_3$ from $CCl_2=CCl_2$ according to variant a) is very particularly preferred. The molar ratio of $CCl_2=CCl_2$ to hydrogen fluoride is preferably from 1:3 to 1:100.

As already noted above, the molar ratio of metal halide to sulfonic acid derivative in the method of the invention must be from about 100:1 to 1:10. If the proportion of sulfonic acid derivative in the catalyst mixture rises above this value, the selectivity decreases, particularly with respect to the preparation of ethane derivatives containing trifluoromethyl groups. If the proportion of sulfonic acid derivative in the catalyst mixture drops below this value, the conversion to higher fluorinated products decreases to unacceptable levels.

Advantageously, the molar ratio of metal halide to sulfonic acid derivative lies in the range from 10:1 to 1:3, particularly advantageously from 2:1 to 1:2.

As stated above, the molar ratio of starting compound to catalyst mixture is from 10:1 to 1:100. In this case the number of moles of the catalyst mixture is calculated by adding the number of moles of metal halide and the number of moles of sulfonic acid derivative. If for instance 1 mole starting compound is reacted with hydrogen fluoride in the presence of a mixture of 0.5 mole niobium pentahalide and 0.5 mole fluorosulfonic acid, the molar ratio of starting compound to catalyst mixture in this case is 1:1.

Preferably the molar ratio of starting compound to catalyst mixture is from 10:1 to 1:10, particularly preferably from 2:1 to 1:5.

Preferably fluorosulfonic acid or trifluoromethane sulfonic acid, particularly preferably fluorosulfonic acid, is used as the sulfonic acid derivative.

Preferably niobium pentahalide, tantalum pentahalide or a mixture thereof is used as the metal halide, wherein halide denotes fluoride, chloride or bromide. Particularly preferably, niobium pentachloride or tantalum pentachloride is used as the metal halide. Excellent results have been obtained using catalyst mixtures comprising niobium pentachloride or tantalum pentachloride and fluorosulfonic acid.

A very particularly preferred embodiment of the method is characterized in that for preparing $CHCl_2CF_3$, the starting compound $CCl_2=CCl_2$ is reacted with at least one-fold the quantity of hydrogen fluoride stoichiometrically required for hydrogen fluoride addition and for the chlorine-fluorine exchange on the alkene, in the presence of a catalyst mixture of niobium pentahalide, tantalum pentahalide or a mixture thereof and of fluorosulfonic acid.

In the method according to the invention, moisture has a disruptive effect. The reaction is therefore advantageously carried out under conditions which prevent a harmful amount of water from entering the reaction mixture. Substantially anhydrous hydrogen fluoride is used. Depending on the quantity of hydrogen fluoride used, it may be recommended to dry the commercially available hydrogen fluoride before use. Furthermore, it is recommended to keep the apparatus used in as dry a condition as possible. For this purpose, lines, reaction vessels, apparatus for working up and storing products may be rinsed with dry gases, for instance with dry air or dry nitrogen gas.

The reaction may be carried out in a batch process or continuously. The reaction mixture may be worked up by passing the reaction products through a gas scrubber and subsequently fractionally distilling the products.

The apparatus used for performing the method should be resistant to hydrogen fluoride, metal halides and the respective sulfonic acid derivative used. Advantageously, components made of teflon and special alloys such as "Hastelloy", a hydrogen fluoride-resistant nickel alloy, are used.

The present invention also relates to a catalyst mixture which can be used in the method according to the invention. The catalyst mixture according to the invention comprises a mixture of metal halide and a sulfonic acid derivative in a molar ratio of 100:1 to 1:10, with the metal halide being selected from the group consisting of niobium pentahalide, tantalum pentahalide, molybdenum pentahalide and mixtures thereof, and the sulfonic acid derivative being selected from the group consisting of fluorosulfonic acid and perfluoro-lower alkane sulfonic acids containing 1 to 4 carbon atoms, in particular trifluoromethane sulfonic acid.

A person skilled in the art can prepare this catalyst mixture by simply mixing the constituents.

A preferred catalyst mixture according to the invention can be obtained by mixing molybdenum pentahalide, tantalum pentahalide or niobium pentahalide, in particular the chlorides or bromides, with a sulfonic acid derivative and hydrogen fluoride. The hydrogen fluoride is advantageously added in such a quantity that no more hydrogen chloride or hydrogen bromide is released.

A particularly preferred catalyst mixture comprises metal halide and sulfonic acid derivative in a molar ratio of approximately 10:1 to 1:3, in particular 2:1 to 1:2.

Very particularly preferred catalyst mixtures comprise a mixture of niobium pentahalide, tantalum pentahalide or a mixture thereof as the metal halide and fluorosulfonic acid, trifluoromethane sulfonic acid or a mixture thereof as the sulfonic acid derivative.

Catalyst mixtures which comprise a mixture of niobium pentahalide or tantalum pentahalide and fluorosulfonic acid yield excellent results in the method of the invention.

Especially preferred catalyst mixtures according to the invention can be obtained by mixing niobium pentachloride or tantalum pentachloride and fluorosulfonic acid and reacting this mixture with hydrogen fluoride until the release of hydrogen chloride has ended.

The invention further relates to hydrogen fluoride solutions for use in the method according to the invention, which contain 0.01 to 99.99% by weight, preferably 10 to 90% by weight, and particularly preferably 30 to 70% by weight, of the catalyst mixture according to the invention. These hydrogen fluoride solutions can be obtained by mixing the metal halide and the sulfonic acid derivative in the required quantity of hydrogen fluoride and optionally separating any hydrogen chloride or hydrogen bromide formed.

The fluorine-containing ethane derivatives produced by the method of the invention are valuable, environmentally compatible solvents, propellants and intermediate products for chemical synthesis.

The method according to the invention is distinguished by high conversion and high selectivity, and it can advantageously be performed in the liquid phase.

The high effectiveness of the method according to the invention must be viewed as surprising and unexpected. For instance, if perchloroethylene is used as the starting compound and pure trifluoromethane sulfonic acid is used as the catalyst, the conversion is low, and partial polymerization of the starting compound is observed. When using fluorosulfonic acid as the catalyst, the yield is insignificantly small. Molybdenum pentachloride as the catalyst does give a very high degree of conversion. However, the formation of higher fluorinated products such as R123 takes place only to a very limited extent, and furthermore the expensive catalyst becomes unusable after only a single performance of the experiment. Niobium pentachloride as a catalyst yields lower degrees of conversion. It was therefore completely unexpected that the combination of these catalyst constituents, which individually are practically unusable, in the method according to the invention should lead to such good results with respect to the degree of conversion, selectivity and life of the catalyst mixture and also permits the preparation of higher fluorinated products, such as in particular R123.

The following examples are intended to explain the method according to the invention in greater detail, without restricting its scope.

EXAMPLES

All the experiments were carried out in the same apparatus. The reaction was carried out in a laboratory autoclave of V4A steel (a steel alloyed with chromium, nickel and molybdenum). The internal volume of this autoclave was 0.25 liters. The autoclave was equipped with a magnetic stirrer, an immersion tube through which it was possible to meter in the starting compounds, and a thermoadapter, by means of which it was possible to measure the internal temperature. The laboratory autoclave also had a gas outlet, which was connected to a gas scrubber filled with water. The gas scrubber was in turn connected to a low-temperature condensation apparatus.

General method for performing the experiments for Examples 1 to 5

The metal halide, the sulfonic acid derivative and the halogenated hydrocarbon used were introduced into the autoclave via the immersion tube with the aid of a metering pump. Then the hydrogen fluoride was also metered in via the immersion tube. Evolution of hydrogen chloride was immediately observed, presumably resulting from the reaction of the metal chloride used and hydrogen fluoride. A hydrogen fluoride solution was formed which contained the catalyst mixture. The evolved hydrogen chloride was withdrawn from the laboratory autoclave and conveyed to the gas scrubber, where it was absorbed by the water present therein.

As soon as the evolution of hydrogen chloride which was initially observed had ceased, the laboratory autoclave was closed, heated to the maximum temperature given in the examples, then brought to ambient temperature, resulting hydrogen chloride gas was released, the autoclave was closed and then heated again to the maximum temperature. This heating was effected by means of an oil bath. The maximum temperature was then maintained for 5 hours. Subsequently, the laboratory autoclave was cooled to room temperature (approximately 22° C). The autoclave contents were then brought to ambient pressure, and volatile constituents were passed through the gas scrubber. Hydrogen chloride and hydrogen fluoride present were washed out in the gas scrubber. The crude gas leaving the gas scrubber and consisting substantially of organic compounds was analyzed by gas chromatography. The crude gas leaving the gas scrubber was transferred into a low-temperature condensation unit. If desired, the crude product could be separated further by working up by distillation.

EXAMPLE 1

Preparation of trifluorodichloroethane and difluorotrichloroethane 27 g niobium pentachloride (0.1 mole), 15 g trifluoromethane sulfonic acid (0.1 mole), 40 g tetrachloroethylene (0.24 mole) and 40 g hydrogen fluoride (2.0 mole) were introduced into the autoclave with the aid of the metering pump. Once the initially observed evolution of hydrogen chloride had ended, the autoclave was closed and heated to a maximum temperature of 160° C. The pressure rose to 33 bar absolute. After cooling, the autoclave contents were worked up as described above. Analysis of the remaining, non-volatile reaction residues showed that 100% of the tetrachloroethylene had been reacted.

The gas chromatography analysis of the gas phase yielded the following values:

3.1% by weight $C_2HF_5$; 0.6% by weight $C_2ClF_4$; 50.2% by weight $C_2HCl_2F_3$; 44.3% by weight $C_2HCl_3F_2$; 0.8% by weight $C_2Cl_4F_2$.

The example shows that with niobium pentachloride and trifluoromethane sulfonic acid as catalyst mixture, tetrachloroethylene can be converted under the given conditions into higher fluorinated ethanes, in particular trifluorodichloroethane and difluorotrichloroethane.

EXAMPLE 2

Preparation of trifluorodichloroethane 27 g niobium pentachloride (0.1 mole), 10 g fluorosulfonic acid (0.1 mole), 40 g tetrachloroethylene (0.24 mole) and 40 g hydrogen fluoride (2.0 mole) were introduced into the laboratory autoclave. After release of the initially evolved hydrogen chloride, the autoclave was closed and heated to a maximum temperature of 130° C., whereby the pressure rose to 19 bar absolute. After cooling, the autoclave was brought to normal pressure, and volatile constituents were separated. Analysis of the non-volatile residue showed that 99.9% of the tetrachloroethylene used had been reacted. The volatile constituents were passed through a gas scrubber, and the crude product leaving the gas scrubber was analyzed using gas chromatography. The analysis yielded the following proportions:

0.4% by weight $C_2HF_5$; 0.1% by weight $CHF_3$; 0.8% by weight $C_2HCl_2F_4$; 81.2% by weight $C_2HCl_2F_3$; 16.7% by weight $C_2HCl_3F_2$.

This example shows that when niobium pentachloride and fluorosulfonic acid are used as the catalyst mixture, tetrachloroethylene is converted into trifluorodichloroethane in good yield and with good selectivity.

EXAMPLE 3

Preparation of trifluorodichloroethane from difluorotrichloroethane 5 g niobium pentachloride (0.02 mole), 14 g fluorosulfonic acid (0.14 mole), 33 g difluorotrichloroethane (0.16 mole) and 40 g hydrogen fluoride (2.0 mole) were introduced into the laboratory autoclave. The initially evolved hydrogen chloride was again released. After this initial hydrogen chloride formation had abated, the laboratory autoclave was closed and heated to a maximum temperature of 125° C. The pressure rose to 25 bar absolute. After cooling, the autoclave was brought to normal pressure and volatile constituents were separated. The volatile constituents were passed through the gas scrubber, and the crude product leaving the gas scrubber was analyzed using gas chromatography. The following values were obtained:

0.3% by weight $C_2H_2Cl_2F_2$; 66.7% by weight $C_2HCl_2F_3$; 2.5% by weight $C_2Cl_3F_3$; 30.5% by weight $C_2HCl_3F_2$.

The conversion of difluorodichloroethane was found to be 49.1% by weight.

EXAMPLE 4

Preparation of trifluorodichloroethane and difluorotrichloroethane from fluorotetrachloroethane 5 g niobium pentachloride (0.02 mole), 14 g fluorosulfonic acid (0.14 mole), 36 g fluorotetrachloroethane (0.16 mole) and 40 g hydrogen fluoride (2.0 mole) were introduced into the autoclave. The initially evolved hydrogen chloride was released, and the autoclave was closed and heated to a maximum temperature of 130° C. The pressure rose to 22 bar absolute. The autoclave was cooled to room temperature and brought to ambient pressure. The volatile constituents were passed through the gas scrubber, and the crude product was analyzed using gas chromatography. The following values were obtained:

1.7% by weight $CHF_3$; 2.9% by weight $CHClF_2$; 0.6% by weight $C_2H_2Cl_2F_2$; 46.4% by weight $C_2HCl_2F_3$; 0.8% by weight $C_2Cl_3F_3$; 47.6% by weight $C_2HCl_3F_2$. The degree of conversion was found to be 63.6% by weight. Examples 3 and 4 demonstrate the suitability of the method of the invention for preparing higher fluorinated haloalkanes from correspondingly lower fluorinated haloalkanes.

EXAMPLE 5

Preparation of trifluorochloroethane from trichloroethylene 36 g tantalum pentachloride (0.1 mole), 10 g fluorosulfonic acid (0.1 mole), 32 g trichloroethylene (0.24 mole) and 40 g hydrogen fluoride (2.0 mole) were introduced into the autoclave. The initially evolved hydrogen chloride was released again. After the initial hydrogen chloride formation had abated, the autoclave was closed and heated to a maximum temperature of 140° C., with the pressure rising to 43 bar absolute. After cooling, the autoclave was brought to ambient pressure, and volatile constituents were passed through the gas scrubber. The crude product leaving the gas scrubber was analyzed by gas chromatography. The following values were obtained:

89.0% by weight $C_2H_2ClF_3$; 7.9% by weight $CCl_3F$; 0.4% by weight $C_2HCl_2F_3$; 0.4% by weight $C_2H_2Cl_2F_2$; 2.3% by weight unknowns.

The conversion of trichloroethylene was 100% by weight.

EXAMPLE 6

Semi-continuous preparation of trifluorodichloroethane

In this example, the apparatus described above was used. 36 g tantalum pentachloride (0.1 mole), 10 g fluorosulfonic acid (0.1 mole), 40 g hydrogen fluoride (2 mole) and 40 g tetrachloroethylene (0.24 mole) were introduced into the autoclave before the first heating phase. The initially evolved hydrogen chloride was released. Then a hydrogen fluoride solution was again present which contained the catalyst mixture. The autoclave was then closed and subjected to the first heating phase. For this purpose, the autoclave contents were heated to the temperature given in Table 2 and kept at this temperature during the period given in Table 2. Then the autoclave contents were brought to ambient temperature, and the resulting hydrogen chloride was released. Then a sample of the compounds which were volatile at ambient temperature and normal pressure was taken and analyzed by gas chromatography to determine the organic compounds contained therein. The analysis values, given in % by weight, are given in Table 2.

The autoclave contents were thereafter subjected to the second heating phase. After cooling, the reactor was brought to normal pressure, and this time the entire content of the compounds which were volatile at ambient temperature and normal pressure was released from the reactor and passed through the gas scrubber. The crude product leaving the gas scrubber was analyzed by gas chromatography.

40 g tetrachloroethylene and 40 g hydrogen fluoride were then introduced again into the reactor, in which the catalyst mixture had remained in addition to the nonvolatile organic compounds. The reactor was then subjected to the third heating phase, cooled, resulting hydrogen chloride was released, and then a sample of the organic compounds which were volatile at ambient temperature and normal pressure was analyzed. Thereupon, the reactor was subjected to the fourth heating phase, cooled, and the entire content of compounds which were volatile at ambient temperature and normal pressure were passed from the reactor into the gas scrubber, whereupon the crude product leaving the gas scrubber was again analyzed by gas chromatography.

In this manner, a total of 10 heating phases were carried out. After the first, third, fifth, seventh and eighth heating phases, only the resulting hydrogen chloride was released from the reactor, and samples were taken each time for analysis. Each time after the second, fourth, sixth and ninth heating phases, the total reactor content of compounds which were volatile at ambient temperature and normal pressure was released from the reactor and passed through the gas scrubber, and the crude product leaving the gas scrubber was analyzed.

Correspondingly, after the second, fourth, sixth and ninth heating phases, 40 g hydrogen fluoride and 40 g tetrachloroethylene were introduced each time into the reactor. The catalyst mixture was neither supplemented nor replenished or regenerated during the entire experiment.

The maximum temperature attained in each heating phase, the maximum pressure reached, the time period over which the maximum temperature was maintained, and also the data obtained from the gas chromatographic analysis of the gas phase after each heating phase are compiled in Table 2.

TABLE 2

| Heat. Phase | Max. Temp. (°C.) | Max. Press. (bar) | Time (hour) | $C_2H_2Cl_2F_2$ % | $C_2H_2ClF_3$ % | $C_2HCl_3F_2$ % | $C_2HCl_2F_3$ % |
|---|---|---|---|---|---|---|---|
| 1 | 120 | 39 | 3.0 | 0.1 | 0.2 | 3.6 | 94.7 |
| 2 | 130 | 14 | 5.0 | — | 0.2 | 2.3 | 97.0 |
| 3 | 120 | 35 | 5.0 | — | — | 6.1 | 92.7 |
| 4 | 120 | 17 | 6.0 | 0.1 | 0.1 | 4.0 | 95.2 |
| 5 | 120 | 34 | 7.5 | 0.2 | 0.1 | 14.4 | 84.2 |
| 6 | 120 | 27 | 7.0 | 0.1 | 0.1 | 21.1 | 82.4 |
| 7 | 90 | 10 | 4.0 | — | — | 10.0 | 88.9 |
| 8 | 105 | 11 | 6.0 | — | — | 8.3 | 90.9 |
| 9 | 110 | 11 | 6.0 | — | — | 18.1 | 81.2 |
| 10 | 110 | 11 | 7.0 | 3.5 | — | 16.5 | 79.8 |

"%" means % by weight.

The resulting dichlorotrifluoroethane consisted of R123 and also traces of R123a.

After completion of the tenth heating phase, the overall conversion of tetrachloroethylene was 91% by weight. In the organic part of the reaction residue (48 g) there was 0.8% by weight trifluorodichloroethane, 37.6% by weight difluorotrichloroethane, 37.6% by weight tetrachloroethylene, and also 23.9% by weight fluorotetrachloroethane. This example demonstrates the suitability of the method of the invention for semi-continuous and continuous operation. Due to the stability of the catalyst mixture, the proportion of higher fluorinated ethanes, particularly trifluorodichloroethane and difluorotrichloroethane, is still very good even after a long reaction time.

EXAMPLE 7

Preparation of 1,1,1,2-tetrafluoroethane (R134a) from trifluoroethylene and hydrogen fluoride The apparatus used in this example corresponded in principle to the apparatus used in Examples 1 to 6. Since the trifluoroethylene starting compound is gaseous at standard conditions, it wasn't introduced into the autoclave by a metering pump. The immersion tube leading into the autoclave was connected via shut-off valves with a pressure gas cylinder containing trifluoroethylene. By appropriately opening the valves, gaseous trifluoroethylene from this pressure cylinder could be introduced into the autoclave.

Initially 39.8 g tantalum pentachloride (0.11 mole) and hydrogen fluoride were introduced into the autoclave and reacted to form tantalum pentafluoride quantitatively. Afterwards 23.6 g fluorosulfonic acid (HSO$_3$F) (0.23 mole) were added.

Then 72 g hydrogen fluoride (3,6 mole) were added in liquid form, and 18 g trifluoroethylene (0.22 mole) were forced into the autoclave. The autoclave was closed and maintained for a period of two hours at 110° C. The overpressure was 15 to 17 atmospheres.

Gaseous reaction products then were passed through the gas scrubber and directly analyzed by gas chromatography combined with mass spectrometry (GC-MS analysis). It was found that 99.5% by weight of the gaseous reaction products consisted of tetrafluoroethane (R134a). The reaction products further contained 0.1% by weight water (entrained in the gas scrubber) and 0.4% by weight C$_2$F$_3$H$_3$ (equal amounts of R143 and R143a). The contents of the reactor were worked up hydrolytically. No polymeric products of trifluoroethylene were found.

This example demonstrates that trifluoroethylene can be reacted with hydrogen fluoride according to the present invention to produce R134a without formation of polymers. Even the crude product is so pure that for most uses, further purification would be superfluous.

EXAMPLE 8

Preparation of 1,1,1,2-tetrafluoroethane (R134a) from trifluoroethylene and hydrogen fluoride The procedure corresponded to that described in Example 7. This time, however, the overpressure was only about 14 atmospheres, the reaction temperature was 103° C., and the reaction time was about 1 hour.

| | |
|---|---|
| Starting material: | 20.8 g (0.25 mole) trifluoroethylene |
| | 76 g (3.8 mole) hydrogen fluoride |
| | catalyst (as in Example 7) |
| GC-MS Analysis: | 2.1% water (entrained in the scrubber) |
| | 1.6% 143a |
| | 0.7% 143 |
| | 95.6% R134a. |

Even with a shorter reaction time and milder reaction conditions, the purity of the product is outstanding.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A catalyst mixture comprising a mixture of metal halide and a sulfonic acid derivative in a molar ratio of from 100:1 to 1:10, wherein said metal halide is selected from the group consisting of niobium pentahalide, tantalum pentahalide, molybdenum pentahalide and mixtures thereof, and the sulfonic acid derivative is selected from the group consisting of fluorosulfonic acid and perfluoro-lower alkane sulfonic acids with 1 to 4 carbon atoms.

2. A catalyst mixture according to claim 1, wherein said sulfonic acid derivative is trifluoromethane sulfonic acid.

3. A catalyst mixture according to claim 2 produced by mixing metal halide, sulfonic acid derivative and hydrogen fluoride.

4. A catalyst mixture according to claim 2, wherein the metal halide and the sulfonic acid derivative are present in a molar ratio of from about 10:1 to 1:3.

5. A catalyst mixture according to claim 4, wherein said metal halide and said sulfonic acid derivative are present in a molar ratio of from about 2:1 to 1:2.

6. A catalyst mixture according to claim 2, wherein said metal halide is selected from the group consisting of niobium pentahalide, tantalum pentahalide and mixtures thereof, and said sulfonic acid derivative is selected from the group consisting of fluorosulfonic acid, trifluoromethane sulfonic acid, and mixtures thereof.

7. A catalyst mixture according to claim 6, comprising a mixture of niobium pentahalide or tantalum pentahalide and fluorosulfonic acid.

8. A hydrogen fluoride solution for use in preparing a fluorine-containing ethane derivative corresponding to the formula

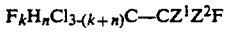

$$F_kH_nCl_{3-(k+n)}C-CZ^1Z^2F \qquad (I)$$

wherein $Z^1$ and $Z^2$ may be identical or different and represent hydrogen, fluorine, chlorine or bromine; k is 0, 1 or 2, and n is 1, 2 or 3, said solution containing from about 0.01 to 99.99% by weight of a catalyst mixture according to claim 16.

* * * * *